(12) United States Patent
Francois et al.

(10) Patent No.: US 10,105,048 B2
(45) Date of Patent: Oct. 23, 2018

(54) POSITION-SENSING CONTACT LENSES

(71) Applicants: Cedric Francois, Crestwood, KY (US); Mark Salman Humayun, Glendale, CA (US)

(72) Inventors: Cedric Francois, Crestwood, KY (US); Mark Salman Humayun, Glendale, CA (US)

( * ) Notice: Subject to any disclaimer, the term of this patent is extended or adjusted under 35 U.S.C. 154(b) by 51 days.

(21) Appl. No.: 15/042,753

(22) Filed: Feb. 12, 2016

(65) Prior Publication Data

US 2017/0086668 A1 Mar. 30, 2017

Related U.S. Application Data

(60) Provisional application No. 62/115,193, filed on Feb. 12, 2015, provisional application No. 62/129,175, filed on Mar. 6, 2015.

(51) Int. Cl.

| | |
|---|---|
| *G02C 7/04* | (2006.01) |
| *A61B 3/113* | (2006.01) |
| *A61B 5/00* | (2006.01) |
| *A61B 3/14* | (2006.01) |
| *A61B 5/11* | (2006.01) |
| *G02C 11/00* | (2006.01) |
| *G02B 1/04* | (2006.01) |
| *A61F 2/16* | (2006.01) |

(52) U.S. Cl.
CPC ............. *A61B 3/113* (2013.01); *A61B 3/145* (2013.01); *A61B 5/0022* (2013.01); *A61B 5/1121* (2013.01); *A61B 5/1128* (2013.01); *A61B 5/6821* (2013.01); *A61F 2/1601* (2015.04); *G02B 1/043* (2013.01); *G02C 11/10* (2013.01); *A61B 2562/028* (2013.01); *A61B 2562/0219* (2013.01); *A61B 2562/0223* (2013.01); *A61B 2562/168* (2013.01); *A61F 2250/0002* (2013.01); *G02C 2202/16* (2013.01)

(58) Field of Classification Search
CPC .................................. G02C 7/04; G02C 7/022
USPC ............ 351/159.02, 159.03, 159.04, 159.34, 351/159.38, 159.39, 159.68
See application file for complete search history.

(56) References Cited

U.S. PATENT DOCUMENTS

2014/0327875 A1* 11/2014 Blum .................... A61F 2/1618
351/159.03

OTHER PUBLICATIONS

Qi Zhou et al, "Electro-Osmotic Dispersion in a Circular Take with Slip-Stick Striped Wall"; Fluid Dyn. Res. vol. 47, No. 1 (2015).
Strook et al, "Controlling Flows in Microchannels with Patterned Surface Charge and Topography"; Acc. Chem. Res 2003, 36, 597-604.
Lap Wing Hau, "Electrokinetically-Driven Liquid Flows in Microchannels Using Surface-Chemistry Technology"; Thesis (Ph.D); Hong Kong University of Science and Technology, 2005.

(Continued)

*Primary Examiner* — Hung Dang
(74) *Attorney, Agent, or Firm* — Dinsmore & Shohl LLP

(57) ABSTRACT

The subject matter of the disclosure relates generally to a MEMS-based position-sensing system and lenses, for example, contact lenses and intra-ocular lenses, manufactured with the position-sensing system employing one or more angular and/or linear accelerometers and/or pressure transducers and methods for detecting position and motion of an eyeball and/or head utilizing the position-sensing contact lenses.

27 Claims, 7 Drawing Sheets

(56) References Cited

OTHER PUBLICATIONS

Wu et al, "Stable Li-Ion Battery Anodes by In-Situ Polymerization of Conducting Hydrogel to Conformally Coat Silicon Nanoparticles"; Nature Communications 4: Article 1943 (2013.
Xie et al, "Grating-Structured Freestanding Triboelectric-Layer Nanogenerator for Harvesting Mechanical Energy at 85% Total Conversion Efficiency"; Advanced Materials 26 (38) 65-99-6607 (2014).

* cited by examiner though it in place. Solid proof masses, however, require containment, have pressure-sensing complexities, and are difficult to manufacture. A simple yet highly sensitive MEMS-based position sensing system capable of fabrication into a contact lens or an intra-ocular lens remains an unmet need in the art.

POSITION-SENSING CONTACT LENSES

PRIORITY CLAIM

This application claims priority to U.S. Provisional Application No. 62/115,193, filed on Feb. 12, 2015 and U.S. Provisional No. 62/129,175, filed on Mar. 6, 2015, the entire disclosures of which are incorporated herein by this reference.

TECHNICAL FIELD

The subject matter of the disclosure relates generally to position-sensing devices and systems. More particularly, in certain embodiments, presented herein are contact lenses for detecting and/or tracking the position of one or both eyes.

BACKGROUND

Contact lenses comprising sensors have a wide variety of applications in, for example, user movement tracking, augmented and virtual reality military and gaming contexts, and medical therapy and rehabilitation. Tangentially, the small size, low power and high volume to cost fabrication of micro electro-mechanical system (MEMS) accelerometers have made them appealing in a wide variety of industries, including robotics and video-gaming. However, most closed loop angular accelerometers operate using a proof mass and measure its displacement or a force required to keep it in place. Solid proof masses, however, require containment, have pressure-sensing complexities, and are difficult to manufacture. A simple yet highly sensitive MEMS-based position sensing system capable of fabrication into a contact lens or an intra-ocular lens remains an unmet need in the art.

SUMMARY

Embodiments described herein make use of micro-accelerometers that substitute microbubbles for a proof mass. In addition to being small, lightweight and inexpensive to manufacture in large quantities, micro-bubble based accelerometers are sensitive to very small accelerations. The most common way to generate a micro-bubble is via creation of hot bubbles from heated resistive wires in an enclosed chamber. With respect to contact lenses, however, convective accelerometers are unsuitable since this would require a heat source located in close proximity to the eye.

Accordingly, in certain embodiments, the present disclosure provides a MEMS-based position-sensing system including a system of 2 or 3 circular fluid-filled micro-channels configured in certain orientations with respect to one another. In some embodiments, the design of the system is somewhat analogous to the vestibular system of the inner ear, suggesting the orientation of the semi-circular canals of the inner ear. In certain embodiments, the fluid comprises a micro-bubble suspended in the fluid such that it seeks restorative equilibrium at the relative apex of the channel. In other embodiments, the channel comprises an element having greater specific gravity than the fluid such that the element seeks restorative equilibrium at the relative nadir of the channel.

Some embodiments provide a MEMS based position-sensing system comprising at least two angular accelerometers, wherein the at least two angular accelerometers comprise a closed substantially toroid (i.e., ring-shaped) fluid-filled channel. The accelerometer channel fluid comprises an inertial element such as at least one microbubble suspended within the fluid, or the channel comprises one or more elements having a specific gravity greater than the fluid. In certain embodiments, the fluid comprises a conductive or semiconductive fluid, and the toroid channel further comprises a sensor for detecting and transmitting acceleration-indicating signal based on motion of the inertial element in the fluid, or motion of the one or more elements having a specific gravity greater than the fluid, relative to the fluid during application of an accelerative force. Each toroid channel is located on a plane unique with respect to other channels.

Certain embodiments provide a MEMS based position-sensing further comprising a linear accelerometer configured to sense force in one, two, or three vectors. In one embodiment, the linear accelerometer comprises a plurality of fluid-filled chambers, for example one to three chambers, each chamber comprising an inertial element (e.g., a ball) and a piezoelectric cantilever. The cantilever senses force of the inertial element against the cantilever, such that each chamber measures acceleration in a vector distinct from the other chambers. In another embodiment, the linear accelerometer comprises a single fluid-filled chamber comprising an inertial element and a plurality of piezoelectric cantilevers, for example, three cantilevers, wherein each cantilever senses force in a vector distinct from the other cantilevers. In such an embodiment, the single chamber measures acceleration in a plurality of vectors. The skilled artisan will appreciate that the number of chambers and/or cantilevers can be adjusted to meet the needs of the particular application.

In another embodiment, the position-sensing contact lens further comprises a camera integrated into the scleral region of the contact lens, wherein the camera senses the horizon and provides additional feedback to calibrate lens position.

According to other embodiments, a position-sensing contact lens comprising an optical region and a scleral region is provided. The optical region is sized to substantially cover a pupil of a wearer of the contact lens, and the scleral region is concentric about the optical region. In some embodiments, at least two angular accelerometers are integrated into the scleral region of the contact lens, the location of each angular accelerometer having an approximately equal radial distance and being spaced an approximately equal distance from one another about an inner circumference of the lens. The angular accelerometers comprise a closed substantially toroid fluid-filled channel and at least one inertial element, for example a microbubble, suspended within the fluid. The toroid channel further comprises a sensor for detecting and transmitting acceleration-indicating signal based on motion of the inertial element in the fluid. Each toroid channel is integrated into the lens at an orientation such that each channel lies on a plane unique with respect to the other channels when the lens is positioned on an eyeball. In another specific embodiment the position-sensing system is fabricated into an intra-ocular lens.

According to other embodiments, the micro-channel fluid comprises at least one element possessing a specific gravity greater than the fluid, and the toroid channel further comprises a sensor for detecting and transmitting acceleration-indicating signal Further embodiments are directed to systems for tracking an eyeball. The system comprises: at least one position-sensing contact lens according to aspects of the invention for adhering to an eyeball via tear-film adhesion; a detecting/receiving means for detecting/receiving acceleration signals transmitted from the two or more accelerometers; and a computer for processing the acceleration signals into position-indicating output.

Additional embodiments provide methods for tracking an eyeball comprising adhering a position-sensing contact lens according to aspects of the invention to an eyeball via tear-film adhesion; detecting/receiving acceleration signals transmitted from the two or more accelerometers; and processing the acceleration signals into position-indicating output.

Methods for determining angular position of a head in an xyz-coordinate space are also disclosed. The methods comprise adhering a contact lens according to aspects of the invention to each eyeball of the head, providing a computer for processing position-indicating signal output from each lens simultaneously or sequentially, and determining angular position of the head based on differential output of one lens relative to the other.

In a first aspect, the present disclosure relates to a system for sensing ocular position. The system includes two or more structures (e.g., toroidal fluid-filled channels serving as angular accelerometers) integrated within a lens (e.g., a contact lens or intraocular lens), and each of the structures defines a unique plane. The system further includes one or more motion-sensing elements (e.g., inertial elements such as microbubbles) associated with (e.g., integrated within) each of the two or more structures, and one or more detectors (whether integrated within the lens, e.g., semi-permeable membranes located within the toroidal fluid-filled channels, or located external to the lens, e.g. a camera, CCD, or other sensor located outside the lens) for identifying a position and/or movement (e.g., angular acceleration) of each of the one or more motion-sensing elements within the respective structure.

In a further embodiment, one or more detectors are communicatively coupled to a computing device, a processor of the computing device. The processor is configured to receive, from the one or more detection devices, a first measurement corresponding to a first structure (e.g., accelerometer) of the two or more structures, and a second measurement corresponding to a second structure (e.g., accelerometer) of the two or more structures, and determine, based at least in part upon the first measurement and the second measurement, an eye motion parameter (e.g., a position, velocity, acceleration, jerk, jounce, etc.) corresponding to an eye of a wearer of the lens.

In a further embodiment, the eye motion parameter includes a coordinate vector corresponding to a three-dimensional coordinate system (e.g., a Cartesian, polar, cylindrical, spherical, or homogenous coordinate set) representing a position, velocity, acceleration, jerk, or jounce of the eye of the wearer of the lens.

In a further embodiment, the processor of the computing device is further configured to calculate, based at least in part upon two eye motion parameters corresponding to two different eyes, a position of a head of the wearer of the lens (e.g., by determining angular position of the head based on differential output of one lens relative to the other).

In a further embodiment, the two or more structures include at least two angular accelerometers integrated into a substantially non-optical (e.g., scleral) region of the lens. The locations of each angular accelerometer are at an approximately equal radial distance and are spaced an approximately equal distance from one another about an inner circumference of the lens. The at least two angular accelerometers each comprises a closed, substantially toroidal fluid-filled channel including at least one inertial element (e.g., a microbubble) suspended within a fluid, and each toroidal fluid-filled channel is integrated into the lens at an orientation such that each channel lies on a plane unique with respect to the other channels when the lens is worn.

In a further embodiment, the one or more structures each include two membranes. The membranes are permeable by the fluid, but not the inertial element, and are oriented in the channel such that the inertial element is bounded within an arc of the toroid fluid-filled channel.

In a further embodiment, the processor of the computing device is configured to calculate, from a first measurement corresponding to a first structure (e.g., accelerometer) of the two or more structures, based at least in part upon a mass of an inertial element corresponding to the first structure and an elasticity of a first membrane corresponding to the first structure, a first angular acceleration of the eye of the wearer of the lens respective to the plane defined by the first structure. The processor calculates, from a second measurement corresponding to a second structure (e.g., accelerometer) of the two or more structures, based at least in part upon a mass of an inertial element corresponding to the second structure and an elasticity of the first membrane corresponding to the second structure, a second angular acceleration of the eye of the wearer of the lens respective to the plane defined by the second structure, and converts the first and second angular accelerations to the eye motion parameter of the eye of the wearer of the lens.

In a further embodiment, the one or more detection devices each include a pressure sensor. The pressure sensor is oriented along a first membrane of the two membranes such that contact pressure upon the first membrane by the inertial element produces a detectable measurement by the pressure sensor.

In another embodiment, the one or more detectors each include a pressure sensor. The pressure sensor is oriented along one of the toroid fluid-filled channels such that contact pressure upon the inner surface of the channel by the inertial element produces a detectable measurement by the pressure sensor.

In another embodiment, the one or more detectors each include a distortion sensor (e.g., a piezoelectric film). The distortion sensor is oriented along a first membrane of the two membranes such that a distortion of the first membrane by the inertial element produces a detectable voltage measurement in the distortion detector.

In another embodiment, a resistive coil is wound around the toroid fluid-filled channels to measure displacement of charged liquid and/or charged inertial element(s).

In a further embodiment, the inertial element is a microbubble. In a further embodiment, the inner surface of the channel is micro-etched to control shear forces acting on the inertial element during accelerations.

In a further embodiment, the two or more structures are individually encased in a polymer compatible with a contact lens polymer from which the contact lens is fabricated, said encasing polymer being substantially impermeable to oxygen. In a further embodiment, the encasing polymer is poly(methyl methacrylate).

In a further embodiment, the planes defined by each of the structures are oriented so that none of the orthogonal axes intersect. In another embodiment, the planes defined by each of the structures are oriented so that at least two of the orthogonal axes intersect. In another embodiment, the system includes a third structure integrated within a lens, the third structure defining a plane unique with respect to the other planes.

In a further embodiment, the at least two accelerometers are micro-machined into a lens polymer from which the lens is fabricated.

In a further embodiment, the lens includes a first (e.g., adhesion) layer, which is permeable by oxygen, and a second (e.g., accelerometer) layer that has the one or motion sensors integrated within. The lens includes an array of microstructures (e.g., pillars) attached to the first layer and the second layer, which form a space between the first and second layers for oxygen to pass and includes an oxygen-permeable seal enclosing the space between the first and second layers. In another embodiment, the second layer is not permeable by oxygen. In a further embodiment, the second layer comprises elements subject to corrosion. In a further embodiment, the first layer adheres to the eye of the wearer of the lens by tear film adhesion.

In a further embodiment, the one or more structures and/or motion-sensing elements comprise MEMS devices.

In another aspect, the present disclosure relates to a system for tracking an eyeball. The system includes at least one position-sensing lens (e.g., contact lens) according to any of the preceding embodiments for adhering to an eyeball via tear-film adhesion. The system includes a detecting/receiving means for detecting/receiving acceleration signals transmitted from the two or more accelerometers and a computer for processing the acceleration signals into position-indicating output.

In another aspect, the present disclosure relates to a system for tracking an eyeball. The system includes at least one position-sensing lens according to any of the preceding embodiments. The system includes a detecting/receiving means for detecting/receiving pressure signals transmitted from the pressure transducer; and a computer for processing the pressure signals into position-indicating output.

In another aspect, the present disclosure relates to a method for tracking an eyeball. The method includes adhering a position-sensing contact lens according to any of the preceding embodiments to an eyeball via tear-film adhesion. The method includes detecting/receiving acceleration signals transmitted from the two or more accelerometers; and processing the acceleration signals into position-indicating output.

In another aspect, the present disclosure relates to a method for tracking an eyeball. The method includes adhering a position-sensing contact lens according to any of the preceding embodiments to an eyeball via tear-film adhesion. The method includes detecting/receiving acceleration and pressure signals transmitted from the two or more accelerometers and corresponding pressure transducers, and processing the acceleration and pressure signals into position-indicating output.

In another aspect, the present disclosure relates to a position-sensing contact lens. The lens includes an optical region and a scleral region. The optical region is sized to substantially cover a pupil of a wearer of the contact lens, with the scleral region concentric about the optical region. The lens includes three angular accelerometers integrated into the scleral region of the contact lens. The location of each of the angular accelerometer are an approximately equal radial distance and are spaced an approximately equal distance from one another about an inner circumference of the lens. Each angular accelerometer includes a closed, substantially toroid fluid-filled channel comprising a microbubble suspended within the fluid, the toroid channel further comprising a sensor for detecting and transmitting acceleration-indicating signals based on movement of the microbubble within the channel, and at least one sensor for detecting and transmitting acceleration-indicating signal based on contact pressure of the microbubble against the inner surface of the channel. Each angular accelerometer is integrated into the lens at an orientation such that each channel lies on a plane unique with respect to the other channels when the lens is adhered to an eyeball. The planes have orthogonal axes, and the planes are oriented such that none of the orthogonal axes intersect.

In another aspect, the present disclosure relates to a position-sensing contact lens. The lens includes an optical region and a scleral region. The optical region is sized to substantially cover a pupil of a wearer of the contact lens, with the scleral region concentric about the optical region. The lens includes at least two angular accelerometers integrated into the scleral region of the contact lens. The location of the angular accelerometers are an approximately equal radial distance and are spaced an approximately equal distance from one another about an inner circumference of the lens. The at least two angular accelerometers include a closed substantially toroid fluid-filled channel. The fluid includes at least one element possessing a specific gravity greater than the fluid. The toroid channel further includes a sensor for detecting and transmitting acceleration-indicating signal, and each toroid channel is integrated into the lens at an orientation such that each channel lies on a plane unique with respect to the other channels when the lens is positioned on an eyeball. In a further embodiment, the element possessing a specific gravity greater than the fluid is a microparticle, and acceleration-indicating signals are generated from the relative motion of the microparticle relative to the fluid in response to movement of the eyeball. In another embodiment, the element possessing a specific gravity greater than the fluid is a second fluid, and acceleration-indicating signals are generated from the relative motion of the two fluids in response to movement of the eyeball.

In another embodiment, the position-sensing contact lens further comprises a camera integrated into the scleral region of the contact lens, wherein the camera senses the horizon and provides additional feedback to calibrate lens position.

In another embodiment, the element possessing a specific gravity greater than the fluid is a plurality of magnetic elements capable of forming a detectable magnetic field or detectably interfering with a magnetic field. In a further embodiment, the plurality of magnetic elements include a ferromagnetic material. In a further embodiment, the ferromagnetic material is selected from Iron (Fe), Cobalt (Co), and Nickel (Ni), or Fe, Co or Ni alloyed with at least one of Fe, Co, Ni, Boron (B), Titanium (Ti), Zinc (Zn), Chromium (Cr), Vanadium (V), Copper (Cu), Scandium (Sc), Manganese (Mn) and Neodymium (Nd). In a further embodiment, the ferromagnetic material is a neodymium-iron-boron alloy.

In another aspect, the present disclosure relates to a method for determining angular position of a head in an xyz-coordinate space. The method includes adhering a contact lens according to any of the above embodiments to each eyeball of the head. The method includes providing a computer for processing position-indicating signal output from each lens simultaneously or sequentially, and determining angular position of the head based on differential output of one lens relative to the other.

In another aspect, the present disclosure relates to a contact lens comprising at least two layers. The layers are separated by a space. The contact lens includes a first layer, intended to adhere to an eyeball via tear film. The first layer is permeable to oxygen. The contact lens includes a second layer. The second layer is impermeable to oxygen. The space between the first layer and second layer permits free access of oxygen molecules to and from the first layer. In a further embodiment, the second layer comprises elements subject to corrosion. In a further embodiment, the elements subject to corrosion are selected from electronic and micro electromechanical system elements such as microchannels, sensors, transmitters and processors. In another embodiment, the space forms a circumferential opening between the two layers and the opening is covered by an oxygen-permeable polymeric seal. In another embodiment, the space is formed from a plurality of micro-pillars adheredly connecting an inner surface of the second layer to an outer surface of the first layer.

In another aspect, the present disclosure relates to a MEMS based position-sensing system including at least two angular accelerometers. The at least two angular accelerometers include a closed substantially toroid fluid-filled channel with at least one microbubble suspended within the fluid. The fluid is a conductive or semiconductive fluid. The toroid channel further includes a sensor for detecting and transmitting acceleration-indicating signals based on motion of the inertial element in the fluid. Each toroid channel is located on a plane unique with respect to other channels. In a further embodiment, the unique planes are oriented so that none of the orthogonal axes intersect. In another embodiment, the system includes three angular accelerometers. The accelerometers are positioned in the system such that they do not touch.

In another aspect, the present disclosure relates to a MEMS based position-sensing system including at least two angular accelerometers. The at least two angular accelerometers include a closed substantially toroid fluid-filled channel, and the fluid includes at least one element possessing a specific gravity greater than the fluid. The toroid channel further includes a sensor for detecting and transmitting acceleration-indicating signal. Each toroid channel is positioned at an orientation such that each channel lies on a plane unique with respect to the other channels. The at least one element possessing a specific gravity greater than the fluid is selected from one or more microparticles, one or more magnetic elements, or a fluid.

In a further embodiment, the present disclosure relates to an intraocular lens including any of the MEMS-based positioning systems herein described.

These and other embodiments will be further detailed and clarified by reference to the drawings and detailed description.

DETAILED DESCRIPTION

Figure 1A:
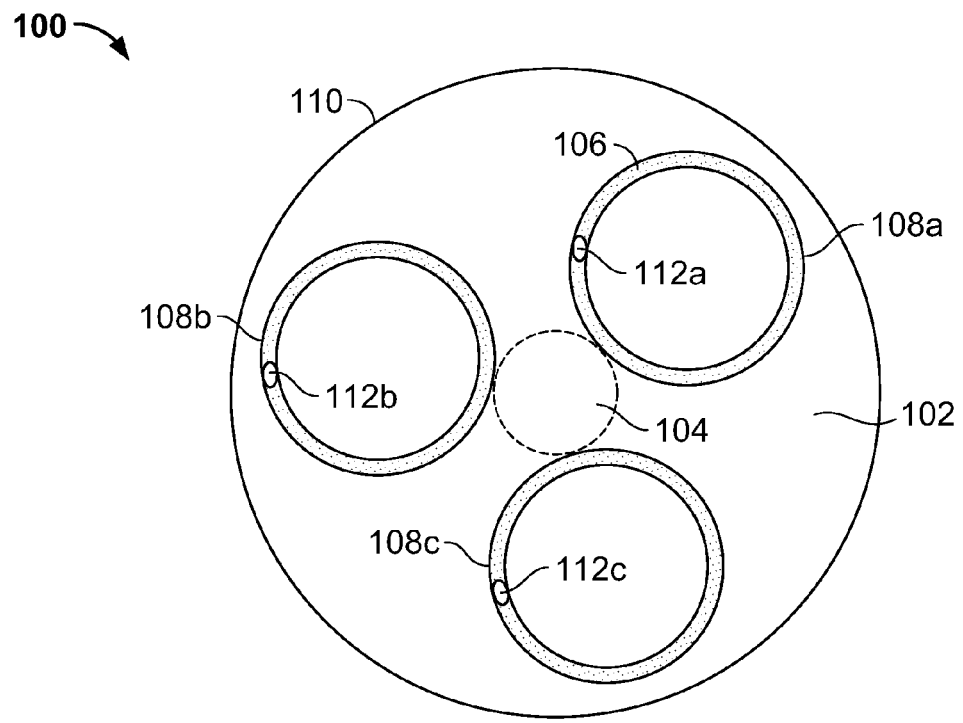
FIG. 1A shows a front view of a lens having three circular micro-channels positioned in the scleral area of the lens, according to an embodiment of the present disclosure.

Described herein are various configurations of a position-sensing contact lens. Certain embodiments provide a communicative interface with the processor of a computer, whereby relative and/or absolute motion or position of an eyeball of a wearer of a position-sensing contact lens is tracked. In further embodiments, the position and/or motion information is sent to a computer program interface or other electronic module. In some embodiments, this information is used to facilitate various user movement tracking, augmented and virtual reality military and gaming applications, and medical therapy and rehabilitation applications. Headers are presented for the convenience of the reader; they are not intended to be limiting.

Position-Sensing Contact Lens

Described herein are various embodiments of a position-sensing contact lens comprising two or more structures integrated within a lens (e.g., a contact lens or intraocular lens), wherein each of the structures define a plane, one or more motion-sensing elements associated with (e.g., integrated within) each of the two or more structures, and one or more detectors for identifying a position and/or movement (e.g., angular acceleration) of each of the one or more motion-sensing elements within the respective structure are discussed. In exemplary embodiments of the present disclosure, two or more toroid fluid-filled microchannel structures each comprise an inertial element (e.g., a microbubble) or charged fluid. The movement of the inertial elements or charged fluid in the microchannel structures are detected to provide position and/or movement information (e.g., angular acceleration). Because each of the structures defines a unique plane with respect to the other structures, these angular accelerations may be combined (e.g., by the processor of a computing device) to provide movement information substantially describing the movement of the eyeball of the wearer of the lens. To complement the angular movements of the lens, linear accelerometers can be added to the structure. In such an embodiment, an inertial element is placed in a micro-manufactured box that senses linear forces in each of the three dimensions (one box linear accelerometer). For example, piezo cantilevers can be placed on three of the six sides of the box to cover the three spatial dimensions. In another embodiment, three inertial elements can be placed in three separate boxes (three-box linear accelerometer), each capturing one of the spatial dimensions (i.e., each box would contain one piezo cantilever).

In a first exemplary embodiment, the configuration of the structures of the position-sensing system of the disclosure is designed as an analog of the vestibular structure of the inner ear, which includes three labyrinth semicircular canals (posterior, lateral and superior) that interface with the cupula providing a basis for response to angular accelerations of the head. Each canal of the vestibular system forms a different plane, and the three planes are at oblique angles to one another. The system is sensitive to angular accelerations about axes orthogonal to each plane. Linear accelerations can be captured by linear accelerometers described prior. The disclosed structures would function in a manner similar to how the inner ear captures linear accelerations using the otoliths.

Turning to FIG. 1A, a position-sensing contact lens comprises an optical region 104 and a scleral region 102. The optical region is sized to substantially cover the pupil of particular wearer of the contact lens, and the scleral region is concentric about the optical region. At least two angular accelerometers are integrated: typically into the scleral region of the contact lens, although in some embodiments there may be some overlap into the optical region. The angular accelerometers are spaced equidistant around an inner circumference of the contact lens and the midpoint of all accelerometer is an approximately equal radial distance from the center point of the lens.

Motion-Sensing Structures

In various embodiments, the angular accelerometers comprise closed substantially toroid fluid-filled channels. The channels may be referred to as a "microchannels" herein. In this case "substantially toroid" includes other shapes ranging from semi-circles to full circles and is intended to convey that geometric precision is not required. Throughout the disclosure, the term "toroid" and "substantially toroid" may be used interchangeably. Microchannel structures may be constructed in shapes from 180° semi-circular channels to 360° circular channels. In other embodiments, microchannel structures may be constructed in non-toroid shapes including linear and freeform shapes. In various embodiments, the orientation of the microchannel structures are roughly parallel to the surface of the lens when worn. In further embodiments, the microchannel structures are oriented to be substantially perpendicular to the surface of the lens (i.e., through the thickness of the lens). In several embodiments, the microchannels are constructed such that the inner surface is micro-etched to control shear forces acting on the inertial element during acceleration.

Figure 1B:
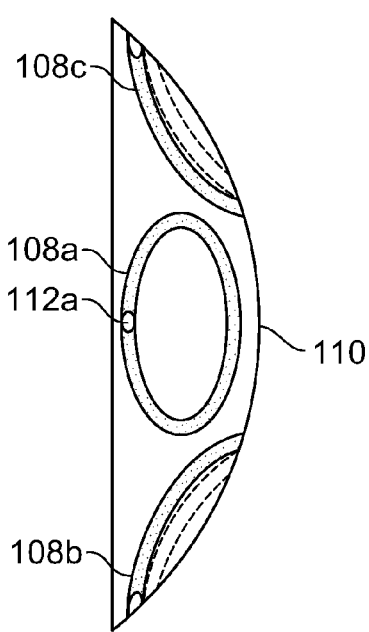
FIG. 1B shows a side view of the lens of FIG. 1A, according to an embodiment of the present disclosure.

Referring back to FIG. 1A, the lens 110 provides three micro-channel structures for position-sensing capabilities (e.g., detecting angular acceleration). The fluid 106 within the micro-channels 108a, 108b, 108c each comprise at least one inertial element 112a, 112b, 112c (collectively, inertial elements 112) suspended within the fluid 106. The channels may further comprise a sensor for detecting and transmitting acceleration-indicating signal based on motion of the inertial element in the fluid. Each toroid channel is integrated into the lens at an orientation such that each channel lies substantially on a plane unique with respect to the planes of the other channels, when the lens is positioned on an eyeball, as depicted in FIG. 1B. A channel may deviate from an entirely planar orientation and still be considered "on a plane."

In specific embodiments the inertial elements 112 are microbubbles. A microbubble moves substantially freely within the fluid in response to accelerations. The equilibrium of a microbubble is the apex of the channel when the lens is located at a particular position in space (e.g., Cartesian, polar, cylindrical, spherical, or homogenous space). When an acceleration is applied, the microbubble moves relative to the fluid. When an acceleration is removed, the microbubble seeks restoration of equilibrium. The movement of the microbubble may be detected by sensors within the channel, or remote from the channel. According to other embodiments, the at least two angular accelerometer aspects each comprise a closed substantially toroid fluid-filled channel and the fluid comprises at least one element possessing a specific gravity greater than the fluid. Optionally, the channel includes one or more sensors for detecting and transmitting acceleration-indicating signals. As with other embodiments, detecting and sensing may be accomplished by remote monitoring. According to these embodiments, the element possessing a specific gravity greater than the fluid seeks an equilibrium position at the nadir of the channel as defined when the contact lens is positioned on an eyeball. Accelerations disturb the equilibrium and the relative movement of the fluid and the element in seeking to restore an equilibrium position provide acceleration-indicating signal which may be processed into position-indicating output.

Figure 7:
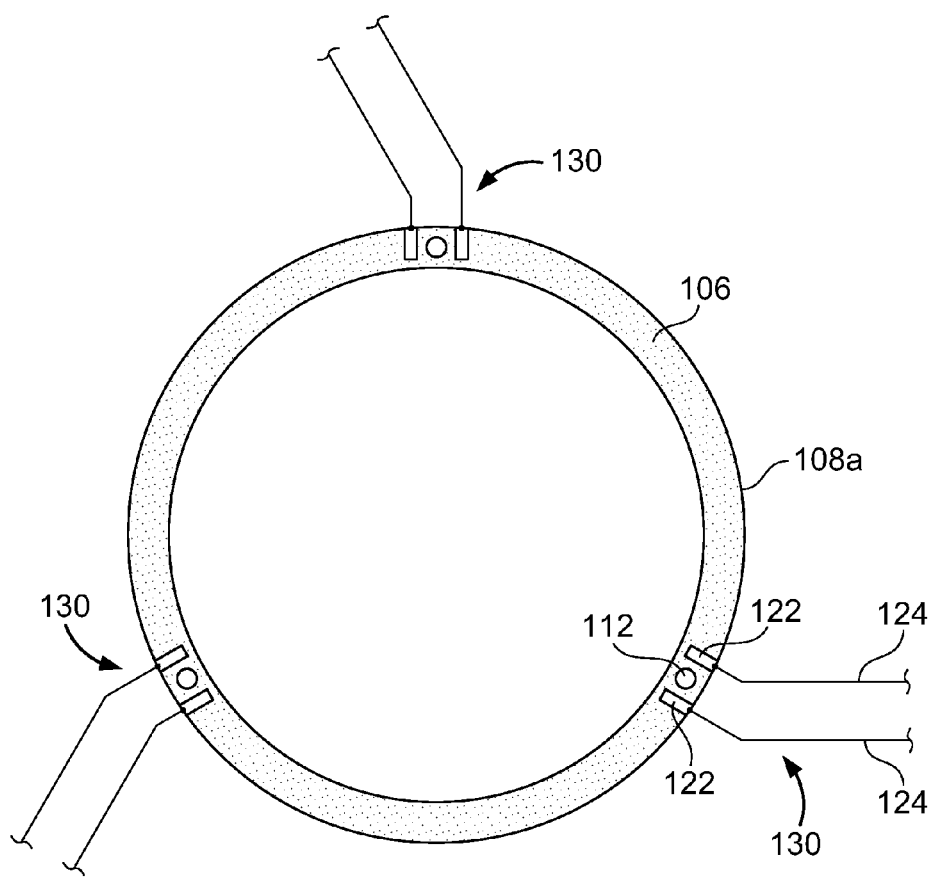
FIG. 7 shows a front view of an exemplary circular micro-channel having three inertial element/cantilever pair assemblies spaced equidistant from one another.

In a specific embodiment depicted in FIG. 7, the toroid channels 108a (shown), 108b, or 108c may contain one or more inertial elements 112, such as a microbubble, each of which is captured between two piezoelectric cantilevers 122. In this embodiment, the motion of the inertial element 112 is sensed by the cantilever pairs, thus measuring angular acceleration. Conducting leads 124 connect the piezoelectric cantilevers 122 to micro-circuitry of the lens (not shown) and permit transfer of the signal from the piezoelectric cantilevers to said micro-circuitry. The embodiment exemplified in FIG. 7 contains three inertial element/cantilever pair assemblies 130, although the skilled artisan will understand that each toroid channel may contain more or less of such assemblies 130.

In other specific embodiments, the element possessing a specific gravity greater than the fluid is a microparticle and the acceleration-indicating signal is generated from the relative motion of the microparticle relative to the fluid in response to movement of the eyeball. In further specific embodiments the element possessing a specific gravity greater than the fluid is a second fluid, and the acceleration-indicating signal is generated from the relative motion of the two fluids in response to movement of the eyeball.

According to another embodiment, the element possessing a specific gravity greater than the fluid is plurality of magnetic elements capable of forming a detectable magnetic field or detectably interfering with a magnetic field. In specific embodiments, the plurality of magnetic elements comprises a ferromagnetic material. The ferromagnetic material is selected from Iron (Fe), Cobalt (Co), and Nickel (Ni), or Fe, Co or Ni alloyed with at least one of Fe, Co, Ni, Boron (B), Titanium (Ti), Zinc (Zn), Chromium (Cr), Vanadium (V), Copper (Cu), Scandium (Sc), Manganese (Mn) and Neodymium (Nd). Super magnet alloys, such as neodymium-iron-boron alloys are particularly suitable. Magnetic sensors are positioned within the magnetic field, for example on glasses, a headband, or around the neck or any other device or accessory intended to be worn near the eyes. In some embodiments, magnetic elements comprise a ferromagnetic material. In embodiments wherein the elements are intended to distort an applied magnetic field, non-magnetic elements are used.

In other specific embodiments each toroid channel further comprises a pressure transducer for detecting/transmitting acceleration-indicating signal based on contact pressure of the microbubble against the inner surface of the channel. In other embodiments, the microbubble are contained within an arc of the channel by two spaced-apart membranes spanning the channel. The membranes are permeable to the fluid such that, upon acceleration, the fluid moves through the membranes. In contrast, the microbubble compresses against one of the membranes. In some embodiments, the contact pressure is detected by pressure sensors on the membrane or by remote sensors, and processed into acceleration and position-indicating output.

Figure 2A:
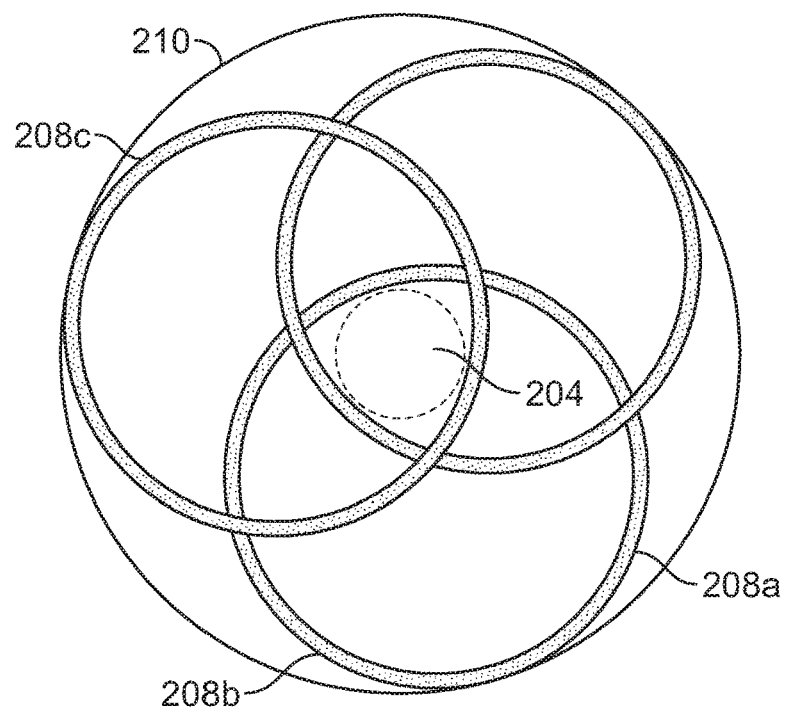
FIG. 2A shows a front view of a lens having three circular micro-channels positioned in the scleral area of the lens, wherein the micro channels overlap, according to an embodiment of the present disclosure.
Figure 2B:
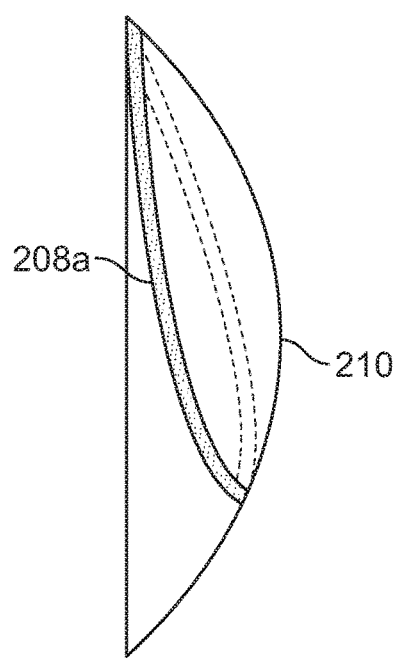
FIG. 2B shows a side view of the lens of FIG. 2A showing one of the three channels, according to an embodiment of the present disclosure.

The orientation of the microchannels relative to one another may vary. The planes formed by the microchannels may be oriented so that none of the orthogonal axes intersect. Such an orientation reflects the exemplary embodiment analogous to the three semi-circular canals of the vestibular system of the inner ear. However, sufficient motion and/or position-indicating output is generated when two or more (or all) of the planes are oriented so that at least two of the orthogonal axes intersect. Further, more than three accelerometers can in some cases yield redundant data, and in other cases greater refinement is effectuated. Such a configuration may be preferred (e.g., to provide redundancy or greater accuracy). Generally, the microchannels do not touch; however in particular embodiments they may apparently overlap from a frontal perspective. For example one microchannel may be positioned partially below or above another. In other embodiments, microchannels may physically intersect allowing fluid to move between channels, forming a continuous space between channels for fluid to flow. FIGS. 2A and 2B depict a front and side view, respectively, of such an embodiment. The lens 210 comprises microchannels 208a, 208b, 208c (collectively, microchannels 208) which, in the front view, appear to overlap. However, as shown in the illustrative FIG. 2B, the microchannel 208a is projected at an angle with respect to the lens, and the microchannels 208 (208b and 208c not depicted) pass near one another without physical intersection. Thusly, the optical region 204 is substantially unobstructed and the microchannels 208 do not physically touch.

In another embodiment, no inertial elements of microbubbles are placed in the fluid of the toroid channels. Instead, a charged fluid is placed in the channel and displacement of the charged fluid is detected by a semiconductive coil wrapped around the channel to measure the displacement of the fluid. In such an embodiment, there is no sensing of gravity. In a specific embodiment, this is compensated by one-box or three-box linear accelerometers placed on the lens.

The microchannels may be fabricated independently of the lens, and then placed in position in the lens during polymerization of the lens polymer, or during some other suitable point in production of the lens. In certain aspects of this embodiment, the accelerometers are individually encased in a polymer compatible with the polymer from which the contact lens is fabricated. The encasing polymer should be substantially impermeable to the fluid and impermeable to substances which may pass through the lens polymer, such as oxygen. It is also preferable that the microchannel be fabricated from a harder polymer to avoid distortion during application of acceleration forces. One exemplary polymer for the encasing is a relatively hard polymer that is no longer used for contact lens fabrication (because it is not permeable to important transfer substances at the eye-environment interface) is poly(methyl methacrylate). According to other specific embodiments, the microchannels may be micro-machined directly into the lens during fabrication of the lens.

According to other embodiments, the microchannel fluid is conductive or semiconductive. In some embodiments the fluid substantially comprises a mixture of water and alcohol; although other substances may be present. Other embodiments are directed to intra-ocular lenses comprising the MEMS-based position-sensing system according to any aspect of the disclosure. An intraocular lens (IOL) is a lens implanted in the eye. Such lenses are well-known in the art and MEMS-based accelerometers may be fabricated into an IOL in a manner similar to fabrication into a contact lens. The IOL may be constructed from a rigid or accommodating polymer. When constructed as an IOL, exposure to oxygen at the corneal interface is not as grave a concern and MEMS elements may be micro-machined directly into the lens. Protection from other corrosive elements may require encasing beyond placement in the lens in some embodiments. Recent research on the fluid mechanics of circular channels and microchannels reveals that certain textures and inner surface constructs may be utilized to control the fluid flow and/or to control shear forces acting on an inertial mass, such as a microbubble, during accelerations. For example, Qi Zhou and Chiu-On Ng "Electro-osmotic dispersion in a circular tube with slip-stick striped wall" *Fluid Dyn. Res.* Vol. 47 No. 1 (2015) demonstrates fluid channel walls periodically micro-patterned along an axial position exhibit alternating slip-stick stripes of distinct zeta potentials. Stroock et al. "Controlling Flows in Microchannels with Patterned Surface Charge and Topography" *Acc. Chem. Res.* 2003, 36, 597-604, is an investigation and comparison of electro-osmotic (EO) and pressure-driven flow in simple channels, and teaches strategies for controlling flows in microchannels, including patterning EO by controlling density of charge on the surface of the microchannel, and patterning PD flow by patterning grooves on the surface of the microchannels, According to these researchers, the ability to pattern flows opens opportunities for new uses of EO and pressure-driven flows in microsystems. With patterns of surface charge density, regions of rotating flow, regions of high and low rates of shear, and stationary points can be positioned with micron-scale precision. These features of the flow could be used to manipulate the position of objects in the flow, generate controlled torques for mechanical actuation, or influence the conformation of macromolecules. By reducing dispersion, the SHM opens the possibility for using pressure-driven flows in MEMS accelerometers. Hau, Lap Wing "Electrokinetically-driven liquid flows in microchannels using surface-chemistry technology" Thesis (Ph.D.)—Hong Kong University of Science and Technology, 2005 illustrates surface-charge patterning technology integrated into the fabrication process of microchannel devices. Three types of microchannel devices were fabricated, with different designs of surface-charge patterns on the channel walls in order to electrokinetically generate three basic flow patterns, namely bi-directional shear flow, out-of-plane vortex and in-plane vortex. This generic surface-charge patterning technology may be applied in construction of the microchannels according to the invention to achieve local control of the liquid motions. The entire disclosures of these publications are incorporated herein by this reference.

In certain embodiments, the systems, lenses, and methods provided herein further comprise a linear accelerometer configured to sense force in one, two, or three vectors. In one embodiment, the linear accelerometer comprises a plurality of fluid-filled chambers, for example one to three chambers, each chamber comprising an inertial element (e.g., a ball) and a piezoelectric cantilever (e.g., three-box linear accelerometer). The cantilever senses force of the inertial element against the cantilever, such that each chamber measures acceleration in a vector distinct from the other chambers. In another embodiment, the linear accelerometer comprises a single fluid-filled chamber comprising an inertial element and a plurality of piezoelectric cantilevers, for example, three cantilevers, wherein each cantilever senses force in a vector distinct from the other cantilevers. In such an embodiment, the single chamber measures acceleration in a plurality of vectors (e.g., one-box accelerometer). The skilled artisan will appreciate that the number of chambers and/or cantilevers can be adjusted to meet the needs of the particular application.

Figure 1C:
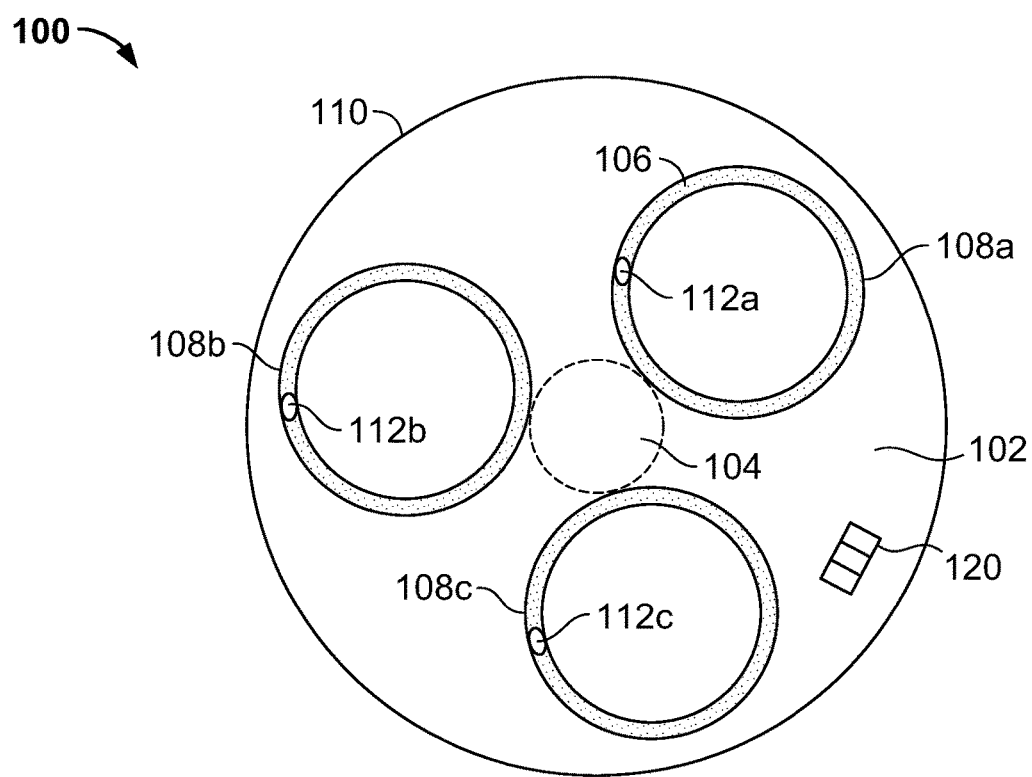
FIG. 1C shows a front view of a lens having three circular micro-channels and a linear accelerometer positioned in the scleral area of the lens, according to an embodiment of the present disclosure.

FIG. 1C depicts an additional embodiment, wherein one or more linear accelerometers 120 are placed in the scleral region 102 of the lens 110. One-box linear accelerometers can be placed at any position where they can easily be integrated into the electrical integrated circuits of the lens. Three-box accelerometers are placed adjacent or non-adjacent to each other at any place in the scleral region of the lens, where they can easily be integrated into the electrical integrated circuits of the lens. FIG. 1C depicts a lens 110 containing both angular accelerometers 108a, 108b, and 108c as well as a three-box linear accelerometer 120, however it is understood that one-box linear accelerometer(s) would be equally useful (not shown).

In another embodiment, the systems, lenses, and methods provided herein further comprise a spherical sensing element, such as a spherical sensing element wherein the interior surface of the sphere comprises a piezoelectric sensor. The spherical sensing element is optionally fluid-filled and comprises an inertial element (e.g., a ball). The spherical sensor is configured to sense the (1) coordinate of the contact point of the inertial element on the interior surface of the sphere and (2) the force of the inertial element on the interior surface of the sphere. These two measurements are combined to determine the acceleration vector.

The purpose of the linear accelerometers is to (1) detect linear acceleration that cannot be detected by angular accelerometers; and (2) detect gravity and which directions are "up" and "down." The linear accelerometers of any of the embodiments described herein can exist on the lens by themselves in the absence of angular accelerometers, or can be combined with angular accelerometers to provide optimal positing sensing. In lenses where linear accelerometers are used in combination with angular accelerometers, the angular accelerometers may lack inertial elements or microbubbles, and may instead contain fluid (charged or non-charged). In one embodiment, the fluid permits sensing of fluid displacement in the toroid channels of the angular accelerometers.

Gas Exchange

Oxygen permeability is a dual concern in the design of contact lenses comprising elements which may corrode upon exposure to oxygen. On one hand, the health of the cornea depends on oxygen and modern contact lenses are oxygen-permeable in order to permit the proper interaction of the eye with oxygen from the air. The cornea draws oxygen from the air and tears act as a dissolving agent. The tears dissolve the oxygen from the air and transport it through the cornea, mimicking the job of blood vessels in other parts of the body. A second gas, carbon dioxide, is a byproduct of the process and is eliminated by the cornea. Interruption of this complex process makes the eye vulnerable to maladies such as corneal scarring, loss of transparency, blood vessels, and corneal warping. On the other hand, micro-electronics are susceptible to the corrosive effects of oxygen and should be protected from oxygen exposure. According to some embodiments, the corrosive elements are encased in an oxygen-impermeable encasement. According to other embodiments, a contact lens comprising at least two layers with a space between the layers that permits substantially free exchange of gasses between the cornea and the atmosphere is provided.

Figure 3:
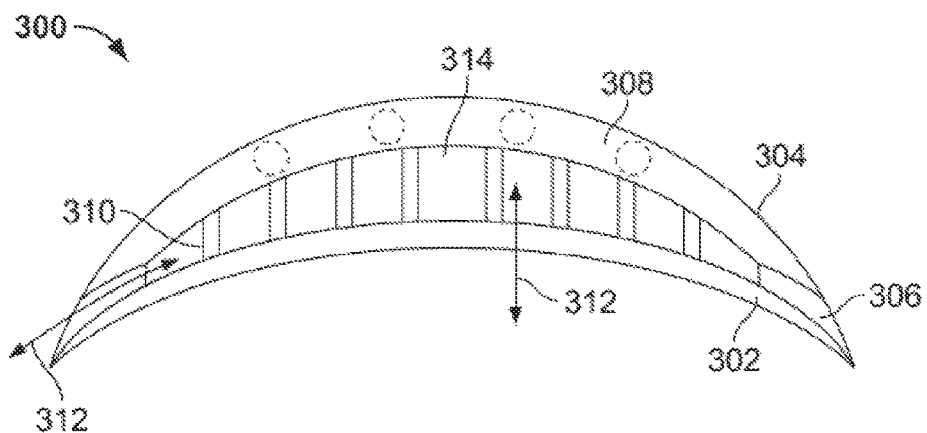
FIG. 3 shows a cut-away side view of a two-layered lens that facilitates ocular gas exchange, according to an embodiment of the present disclosure.

FIG. 3 shows a cut-away side view of a two-layered lens that facilitates ocular gas exchange, according to an embodiment of the present disclosure. The lens 300 comprises a first layer 302 intended to adhere to an eyeball via tear film. and a second layer 304 in which the motion-sensing structures 308, motion-sensing elements, and optionally the detectors are integrated. Potentially corrosive elements, including but not limited to electronic and micro electromechanical system (MEMS) are located in the second layer, which is substantially impermeable to oxygen. A non-exclusive list of such elements includes accelerometers, microchannels generally, pressure transducers, micro-processors, gyroscopic elements, and other sensors and transmitters.

The space 314 forms a circumferential opening between the two layers. In various embodiments, the layers 302, 304 are of substantially uniform thickness. In other embodiments, either or both of the layers 302, 304 are "domed" such that it is thicker in the center, or any desired thickness depending on the functionality and the attributes of the wearer's eye. In specific embodiments, the opening is covered by an oxygen-permeable polymeric seal 306. In certain embodiments, the space 314 is held open by a plurality of micro-pillars 310, the micro-pillars 310 connecting an inner surface of the second layer to an outer surface of the first layer (e.g., by adhesion, welding, or other means of microstructural attachment). The micro-pillars may be formed from a flexible or substantially rigid polymeric material depending on the application, design, and/or composition of the lens.

The first layer 302 is substantially permeable to substances associated with ocular gas exchange 312, such as oxygen and carbon dioxide. Accordingly, substances associated with ocular gas exchange 312 pass freely between the eye of the wearer of the lens and the space 314. Similarly, the seal 306 is oxygen-permeable and provides free flow of substances associated with ocular gas exchange 312 between the environment and the space 314. Thus, the eye can effectively perform gas exchange functions with the environment across the first layer 302 and the seal 306.

Detection Elements

Various embodiments are directed to a system for tracking an eyeball. The system comprises at least one position-sensing contact lens for adhering to an eyeball via tear-film adhesion according to the present disclosure; a detecting/receiving means for detecting/receiving acceleration signals transmitted from the two or more accelerometers; and a computer for processing the acceleration signals into position-indicating output. In other specific embodiments the tracking system may include detecting/receiving means for detecting/receiving pressure signals transmitted from the pressure transducer; and a computer for processing the pressure signals into position-indicating output. Methods for tracking an eyeball are also provided based on utilization of the inventive systems of the disclosure.

Embodiments directed to methods for determining angular position of a head in a three-dimensional coordinate space are also provided (e.g., Cartesian, polar, cylindrical, spherical, or homogenous space). In certain embodiments, the method comprises: adhering a contact lens according to any aspect of the inventive lenses as disclosed to each eyeball of the head, providing a computer for processing position-indicating signal output from each lens simultaneously or sequentially, and determining angular position of the head based on differential output of one lens relative to the other.

According to one embodiment, a MEMS based position-sensing system comprising at least two angular accelerometers is provided. The at least two angular accelerometers comprise a closed substantially toroid fluid-filled channel comprising at least one microbubble suspended within the fluid, wherein the fluid comprises a conductive or semiconductive fluid. The toroid channel further comprising at least one sensor for detecting and transmitting acceleration-indicating signal based on motion of the inertial element in the fluid. The system is constructed as an analog of the vestibular system of the inner ear. Each toroid channel is located on a plane unique with respect to other channels, and in specific embodiments the unique planes are oriented so that none of the orthogonal axes intersect. It is also contemplated that one or more of the orthogonal axes may intersect. In certain embodiments the MEMS based position sensing system comprises three angular accelerometers, wherein the accelerometers are positioned in the system such that they do not touch, although they may overlap so long as they are located on different planes with respect to one another.

In other embodiments, rather than an inertial element or microbubble, the fluid of the angular accelerometers comprises at least one element possessing a specific gravity greater than the fluid. The at least one element possessing a specific gravity greater than the fluid is selected from one or more microparticles, one or more magnetic elements, and a fluid. In another embodiment, no inertial elements or microbubbles are contained in the fluid and only motion of the fluid is sensed by the system to detect angular acceleration without gravity sensing.

Figure 4:
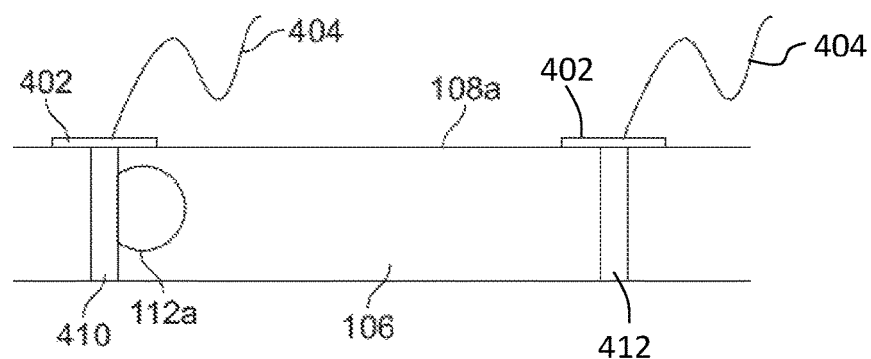
FIG. 4 is a diagram of a fluid-filled microchannel motion-sensing element, according to an embodiment of the present disclosure.

Depending on the motion-sensing elements and/or structures used, detection means vary. FIG. 4 is a diagram of a fluid-filled microchannel motion-sensing element, according to an embodiment of the present disclosure. The fluid-filled microchannel 106 comprises the inertial element 112*a* (e.g., a microbubble). The inertial element 112*a* is bounded in an arc or section of the microchannel by the membranes 410, 412. The channel orientation is configured such that the equilibrium point of the inertial element 112*a* exists at the midpoint between the membranes 410, 412. As the fluid-filled microchannel 108*a* is subjected to an acceleration, the fluid occupying the channel passes freely through the membranes 410, 412. Conversely, the inertial element 112*a* is also accelerated toward, but does not pass through, the membrane 410. As the inertial element 112*a* is pressed against the membrane 410, the membrane 410 experiences a pressure force. The pressure sensor 402 detects the pressure force and produces a measurement (e.g., a voltage change). In other embodiments, the pressure sensor 402 comprises a piezoelectric film rigidly attached to the external wall of the microchannel concentrically with the membrane 410. As the membrane is distorted, the voltage change detected in the piezoelectric film is converted to an acceleration based upon at least the mass of the inertial element and elasticity of the membrane. In other embodiments, detection of the inertial element is performed by a pressure sensor coextensive with at least a portion of the outer wall of the microchannel, able to detect the magnitude of pressure changes relative to one or more points along the toroid fluid-filled microchannel. The pressure sensor detects movement of the inertial element by sensing pressure against the internal wall of the microchannel as the inertial element passes through the channel.

In certain embodiments, the pressure sensor 402 projects the measurement to a computing device via interconnection 404 (e.g., a wire or an antenna). In other embodiments, the measurements are carried by interconnection 404 to a communication module (e.g., the communication module comprising two or more channels, an analog-to-digital converter, and a wireless interconnection module) further integrated within the lens, for example, within the periphery of the lens. In certain embodiments, the pressure sensor 402 further comprises an analog-to-digital conversion module. In certain embodiments, detection is performed remotely from the lens. In some embodiments, the motion-sensing element is a ferromagnetic microparticle. The microparticle produces distortion in an electromagnetic field generated within the general area of the lens. Disturbance in the electromagnetic field is detected by one or more sensors attached to a portable, wearable or fixed-location detector (e.g., a set of glasses, a necklace, or other object capable of including a sensor array). In other embodiments, the motion-sensing element comprises another fluid containing conductive or non-conductive elements, which disturb a magnetic field and cause a measurable distortion.

In certain embodiments, the system further comprises a linear accelerometer configured to sense force in one, two, or three vectors. In one embodiment, the linear accelerometer comprises a plurality of fluid-filled chambers, for example one to three chambers, each chamber comprising an inertial element (e.g., a ball) and a piezoelectric cantilever. The cantilever senses force of the inertial element against the cantilever, such that each chamber measures acceleration in a vector distinct from the other chambers. In another embodiment, the linear accelerometer comprises a single fluid-filled chamber comprising an inertial element and a plurality of piezoelectric cantilevers, for example, three cantilevers, wherein each cantilever senses force in a vector distinct from the other cantilevers. In such an embodiment, the single chamber measures acceleration in a plurality of vectors. The skilled artisan will appreciate that the number of chambers and/or cantilevers can be adjusted to meet the needs of the particular application.

In another embodiment, the system further comprises a spherical sensing element, such as a spherical sensing element wherein the interior surface of the sphere comprises a piezoelectric sensor. The spherical sensing element is optionally fluid-filled and comprises an inertial element (e.g., a ball). The spherical sensor is configured to sense the (1) coordinate of the contact point of the inertial element on the interior surface of the sphere and (2) the force of the inertial element on the interior surface of the sphere. These two measurements are combined to determine the acceleration vector. When linear accelerometers are used in combination with the angular accelerometers, the angular accelerometers may optionally lack microbubbles or inertial elements in the toroid channels; in such an embodiment, the linear accelerometers would compensate for the omitted microbubbles or inertial elements in the toroid channels.

In another embodiment, the position-sensing contact lens further comprises a camera integrated into the scleral region of the contact lens, wherein the camera senses the horizon and provides additional feedback to calibrate lens position.

Computing Environment

Figure 5:
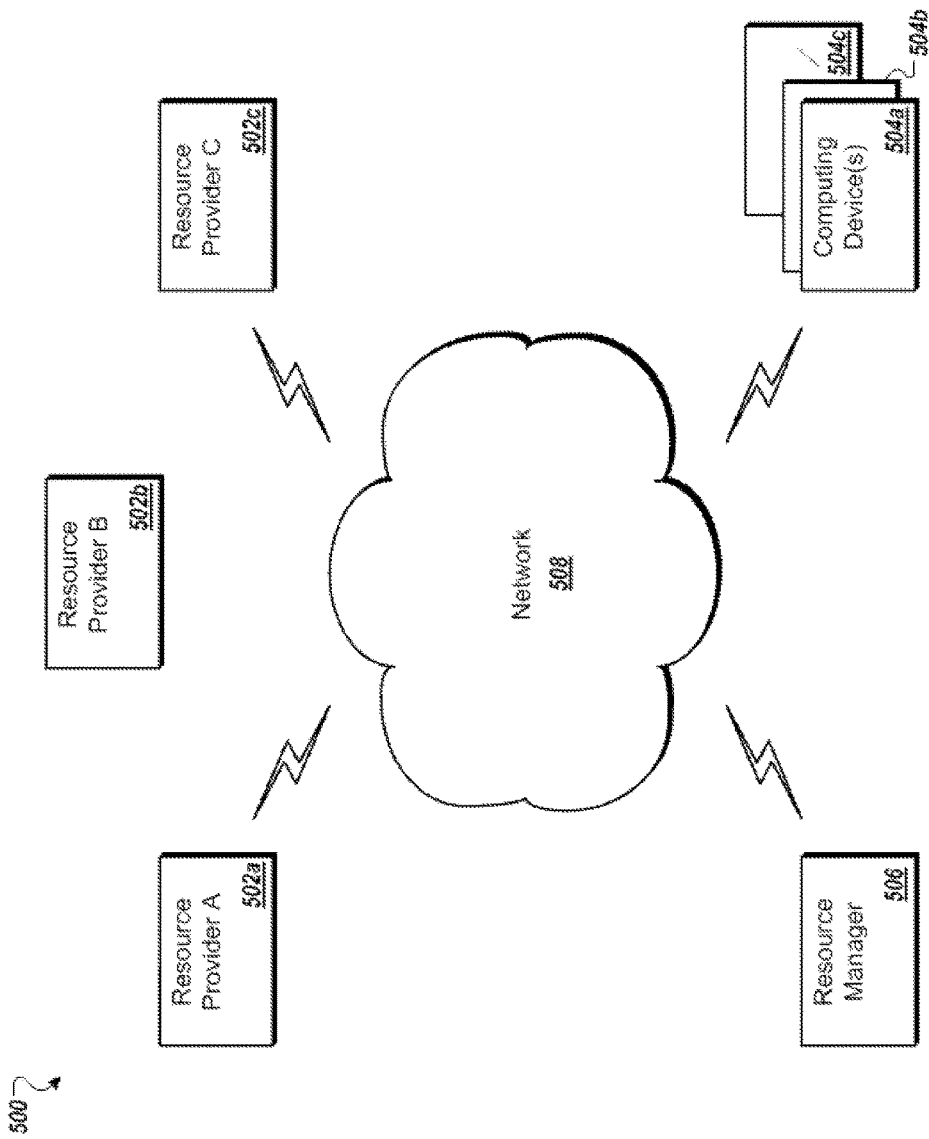
FIG. 5 is a block diagram of an example network environment for use in the methods and systems for a position-sensing lens, according to an embodiment of the present disclosure.

FIG. 5 shows an illustrative network environment 500 for use in the methods and systems for analysis of spectrometry data corresponding to particles of a sample, as described herein. In brief overview, referring now to FIG. 5, a block diagram of an exemplary cloud computing environment 500 is shown and described. The cloud computing environment 500 may include one or more resource providers 502a, 502b, 502c (collectively, 502). Each resource provider 502 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 502 may be connected to any other resource provider 502 in the cloud computing environment 500. In some implementations, the resource providers 502 may be connected over a computer network 508. Each resource provider 502 may be connected to one or more computing device 504a, 504b, 504c (collectively, 504), over the computer network 508.

The cloud computing environment 500 may include a resource manager 506. The resource manager 506 may be connected to the resource providers 502 and the computing devices 504 over the computer network 508. In some implementations, the resource manager 506 may facilitate the provision of computing resources by one or more resource providers 502 to one or more computing devices 504. The resource manager 506 may receive a request for a computing resource from a particular computing device 504. The resource manager 506 may identify one or more resource providers 502 capable of providing the computing resource requested by the computing device 504. The resource manager 506 may select a resource provider 502 to provide the computing resource. The resource manager 506 may facilitate a connection between the resource provider 502 and a particular computing device 504. In some implementations, the resource manager 506 may establish a connection between a particular resource provider 502 and a particular computing device 504. In some implementations, the resource manager 506 may redirect a particular computing device 504 to a particular resource provider 502 with the requested computing resource.

Figure 6:
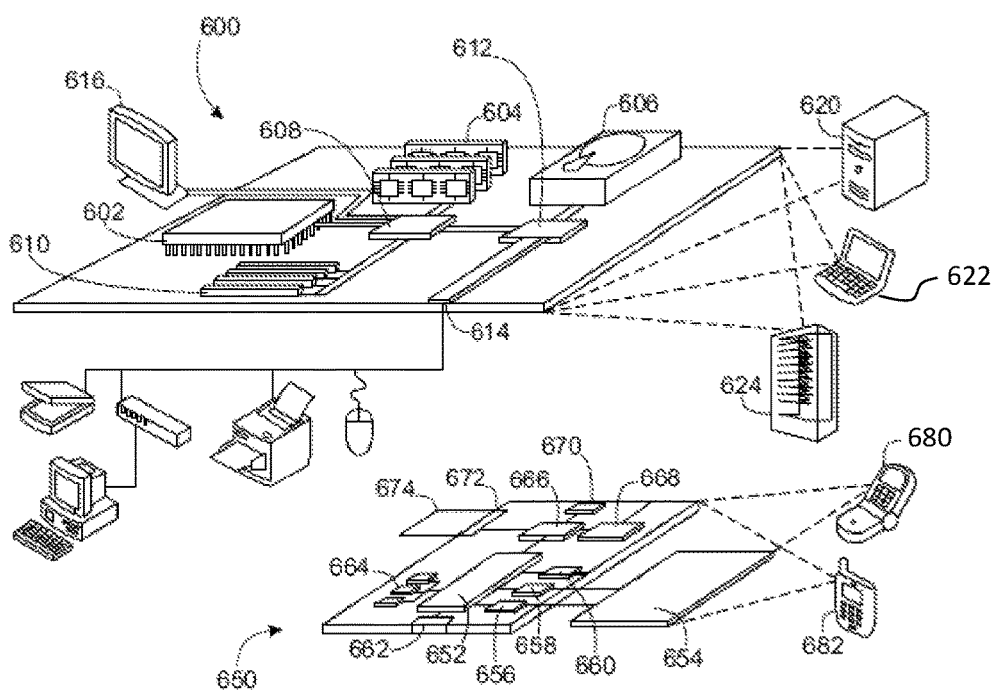
FIG. 6 is a block diagram of an example computing device, according to an embodiment of the present disclosure.

FIG. 6 shows an example of a computing device 600 and a mobile computing device 650 that can be used in the methods and systems described in this disclosure. The computing device 600 is intended to represent various forms of digital computers, such as laptops, desktops, workstations, personal digital assistants, servers, blade servers, mainframes, and other appropriate computers. The mobile computing device 650 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 604 stores information within the computing device 600. In some implementations, the memory 604 is a volatile memory unit or units. In some implementations, the memory 604 is a non-volatile memory unit or units. The memory 604 may also be another form of computer-readable medium, such as a magnetic or optical disk.

The storage device 606 is capable of providing mass storage for the computing device 600. In some implementations, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 602), perform one or more methods, such as those described above. The instructions can also be stored by one or more storage devices such as computer- or machine-readable mediums (for example, the memory 604, the storage device 606, or memory on the processor 602).

The high-speed interface 608 manages bandwidth-intensive operations for the computing device 600, while the low-speed interface 612 manages lower bandwidth-intensive operations. Such allocation of functions is an example only. In some implementations, the high-speed interface 608 is coupled to the memory 604, the display 616 (e.g., through a graphics processor or accelerator), and to the high-speed expansion ports 610, which may accept various expansion cards (not shown). In the implementation, the low-speed interface 612 is coupled to the storage device 606 and the low-speed expansion port 614. The low-speed expansion port 614, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter. The computing device 600 may be implemented in a number of different forms, as shown in the figure. For example, it may be implemented as a standard server 620, or multiple times in a group of such servers. In addition, it may be implemented in a personal computer such as a laptop computer 622. It may also be implemented as part of a rack server system 624. Alternatively, components from the computing device 600 may be combined with other components in a mobile device (not shown), such as a mobile computing device 650. Each of such devices may contain one or more of the computing device 600 and the mobile computing device 650, and an entire system may be made up of multiple computing devices communicating with each other.

The mobile computing device 650 includes a processor 652, a memory 664, an input/output device such as a display 654, a communication interface 666, and a transceiver 668, among other components. The mobile computing device 650 may also be provided with a storage device, such as a micro-drive or other device, to provide additional storage. Each of the processor 652, the memory 664, the display 654, the communication interface 666, and the transceiver 668, are interconnected using various buses, and several of the components may be mounted on a common motherboard or in other manners as appropriate.

The processor 652 can execute instructions within the mobile computing device 650, including instructions stored in the memory 664. The processor 652 may be implemented as a chipset of chips that include separate and multiple analog and digital processors. The processor 652 may provide, for example, for coordination of the other components of the mobile computing device 650, such as control of user interfaces, applications run by the mobile computing device 650, and wireless communication by the mobile computing device 650.

The processor 652 may communicate with a user through a control interface 658 and a display interface 656 coupled to the display 654. The display 654 may be, for example, a TFT (Thin-Film-Transistor Liquid Crystal Display) display or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may provide communication with the processor 652, so as to enable near area communication of the mobile computing device 650 with other devices. The external interface 662 may provide, for example, for wired communication in some implementations, or for wireless communication in other implementations, and multiple interfaces may also be used.

The memory 664 stores information within the mobile computing device 650. The memory 664 can be implemented as one or more of a computer-readable medium or media, a volatile memory unit or units, or a non-volatile memory unit or units. An expansion memory 674 may also be provided and connected to the mobile computing device 650 through an expansion interface 672, which may include, for example, a SIMM (Single In Line Memory Module) card interface. The expansion memory 674 may provide extra storage space for the mobile computing device 650, or may also store applications or other information for the mobile computing device 650. Specifically, the expansion memory 674 may include instructions to carry out or supplement the processes described above, and may include secure information also. Thus, for example, the expansion memory 674 may be provided as a security module for the mobile computing device 650, and may be programmed with instructions that permit secure use of the mobile computing device 650. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 652), perform one or more methods, such as those described above. The instructions can also be stored by one or more storage devices, such as one or more computer- or machine-readable mediums (for example, the memory 664, the expansion memory 674, or memory on the processor 652). In some implementations, the instructions can be received in a propagated signal, for example, over the transceiver 668 or the external interface 662. The mobile computing device 650 may communicate wirelessly through the communication interface 666, which may include digital signal processing circuitry where necessary. The communication interface 666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 668 using a radio-frequency. In addition, short-range communication may occur, such as using a Bluetooth®, Wi-Fi™, or other such transceiver (not shown). In addition, a GPS (Global Positioning System) receiver module 670 may provide additional navigation- and location-related wireless data to the mobile computing device 650, which may be used as appropriate by applications running on the mobile computing device 650. The mobile computing device 650 may also communicate audibly using an audio codec 660, which may receive spoken information from a user and convert it to usable digital information. The audio codec 660 may likewise generate audible sound for a user, such as through a speaker, e.g., in a handset of the mobile computing device 650. Such sound may include sound from voice telephone calls, may include recorded sound (e.g., voice messages, music files, etc.) and may also include sound generated by applications operating on the mobile computing device 650.

The mobile computing device 650 may be implemented in a number of different forms, as shown in the figure. For example, it may be implemented as a cellular telephone 680. It may also be implemented as part of a smart-phone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor. To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Power

Powering the system described in herein can be accomplished in a myriad of ways described in the art. In one embodiment, photovoltaic or induction is the source of power. However, the present disclosure describes a system that will generate an electrical signal through sensing. The excess electricity generated by the sensing can be stored in MEMS batteries or capacitors on the lens for storage and use in the other micro-circuit electrical needs. Batteries can be lithium or silicon storage media. A specific embodiment would be the use of electrodes made of silicon and conducting polymer hydrogel (Wu, et al., "Stable Li-ion battery anodes by in-situ polymerization of conducting hydrogel to conformally coat silicon nanoparticles," *Nature Communications* 4: Article 1943 (2013)). The hydrogel that makes up the portion of the contact lens in touch with the eye could be engineered to contain silicon nanoparticles that would make the contact lens its own electrical storage device. The nanoparticles can be charged photovoltaically or through induction, or through the movement of the lens. This can be accomplished in two ways: (1) the surplus electricity from the accelerometers is captured and stored (e.g., Hu, et al., "Recent progress in piezoelectric nanogenerators as a sustainable power source in self-powered systems and active sensors," *Nano Energy* (2015)) and/or (2) when a person blinks, the friction of the eyelid over the lens produces electricity that can be captured, for example, by triboelectric generators (e.g., Xie, et al., "Grating-Structured Freestanding Triboelectric-Layer Nanogenerator for Harvesting Mechanical Energy at 85% Total Conversion Efficiency," *Advanced Materials* 26(38) 6599-6607 (2014)) and stored in the lens for instant or future use.

A person of ordinary skill in the art will understand that specific attributes of the contact lenses may be altered or adapted without departing from the spirit nor limiting the scope of the instant invention as defined by the claims. The scope of the present invention is not intended to be limited to the above Description, but rather is as set forth in the appended claims. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. It should also be understood that, in general, where the invention, or aspects of the invention, is/are referred to as comprising particular elements, features, etc., certain embodiments of the invention or aspects of the invention consist, or consist essentially of, such elements, features, etc.

What is claimed is:

1. A system for sensing ocular position, the system comprising:
    two or more structures integrated within a lens, each of the structures defining a unique plane;
    one or more motion-sensing elements associated with each of the two or more structures; and
    one or more detectors for identifying a position and/or movement of each of the one or more motion-sensing elements within the respective structure.

2. The system of claim 1, wherein the one or more detectors are communicatively coupled to a computing device, a processor of the computing device configured to:
    receive, from the one or more detectors,
        a first measurement corresponding to a first structure of the two or more structures, and
        a second measurement corresponding to a second structure of the two or more structures; and
    determine, based at least in part upon the first measurement and the second measurement, an eye motion parameter corresponding to an eye of a wearer of the lens.

3. The system of claim 2, the eye motion parameter comprising a coordinate vector corresponding to a three-dimensional coordinate system representing at least one member selected from the group consisting of: a position, velocity, acceleration, jerk, or jounce of the eye of the wearer of the lens.

4. The system of claim 3, wherein the processor of the computing device is further configured to: calculate, based at least in part upon two eye motion parameters corresponding to two different eyes, a position of a head of the wearer of the lens.

5. The system of claim 1, wherein the two or more structures comprise:
    at least two angular accelerometers integrated into a substantially non-optical region of the lens, the location of each angular accelerometer having an approximately equal radial distance and being spaced an approximately equal distance from one another about an inner circumference of the lens;
    wherein the at least two angular accelerometers each comprises a closed substantially toroidal fluid-filled channel comprising at least one inertial element suspended within a fluid, wherein each toroidal fluid-filled channel is integrated into the lens at an orientation such that each channel lies on a plane unique with respect to the other channels when the lens is worn.

6. The system of claim 5, wherein the one or more structures each comprises:
two membranes, the membranes being permeable by the fluid but not the inertial element, oriented in the channel such that the inertial element is bounded within an arc of the toroid fluid-filled channel.

7. The system of claim 6, comprising a processor of a computing device configured to:
calculate, from a first measurement corresponding to a first structure of the two or more structures, based at least in part upon a mass of an inertial element corresponding to the first structure and an elasticity of a first membrane corresponding to the first structure, a first angular acceleration of the eye of the wearer of the lens respective to the plane defined by the first structure;
calculate, from a second measurement corresponding to a second structure of the two or more structures, based at least in part upon a mass of an inertial element corresponding to the second structure and an elasticity of the first membrane corresponding to the second structure, a second angular acceleration of the eye of the wearer of the lens respective to the plane defined by the second structure; and
convert the first and second angular accelerations to the eye motion parameter of the eye of the wearer of the lens.

8. The system of claim 6, wherein the one or more detectors each comprises:
a pressure sensor, the pressure sensor oriented along a first membrane of the two membranes such that contact pressure upon the first membrane by the inertial element produces a detectable measurement by the pressure sensor.

9. The system of claim 6, wherein the one or more detectors each comprises:
a distortion sensor, the distortion sensor oriented along a first membrane of the two membranes such that a distortion of the first membrane by the inertial element produces a detectable voltage measurement in the distortion detector.

10. The system of claim 5, wherein the one or more detectors each comprises:
a pressure sensor, the pressure sensor oriented along one of the toroid fluid-filled channels such that contact pressure upon the inner surface of the channel by the inertial element produces a detectable measurement by the pressure sensor.

11. The system of claim 5, wherein the inertial element is a microbubble.

12. The system of claim 5, wherein an inner surface of the channel is micro-etched to control shear forces acting on the inertial element during accelerations.

13. The system of claim 5, wherein the at least two accelerometers are micro-machined into a lens polymer from which the lens is fabricated.

14. The system of claim 1, wherein the two or more structures are individually encased in a polymer compatible with a contact lens polymer from which the contact lens is fabricated, said encasing polymer being substantially impermeable to oxygen.

15. The system of claim 14, wherein the encasing polymer is poly(methyl methacrylate).

16. The system of claim 1, wherein the planes defined by each of the structures are oriented so that none of the orthogonal axes intersect.

17. The system of claim 1, wherein the planes defined by each of the structures are oriented so that at least two of the orthogonal axes intersect.

18. The system of claim 1, further comprising a third structure integrated within a lens, the third structure defining a plane unique with respect to the other planes.

19. The system of claim 1, wherein the lens comprises:
a first layer, the first layer permeable by oxygen;
a second layer having the one or motion sensors integrated therein;
an array of microstructures attached to the first layer and the second layer, thereby forming a space between the first and second layers for oxygen to pass; and
an oxygen-permeable seal enclosing the space between the first and second layers.

20. The system of claim 19, wherein the second layer is not permeable by oxygen.

21. The system of claim 19, wherein the second layer comprises elements subject to corrosion.

22. The system of claim 19, wherein the first layer adheres to the eye of the wearer of the lens by tear film adhesion.

23. The system of claim 1, wherein one or more structures and/or motion-sensing elements comprises MEMS devices.

24. A system for tracking an eyeball, the system comprising: at least one system for sensing ocular position according to any one of claims 1 to 23 for adhering to an eyeball via tear-film adhesion; a detecting/receiving means for detecting/receiving acceleration signals transmitted from the two or more accelerometers; and a computer for processing the acceleration signals into position-indicating output.

25. A system for tracking an eyeball, the system comprising: at least one system for sensing ocular position according to any one of claims 1 to 23, a detecting/receiving means for detecting/receiving pressure signals transmitted from the pressure transducer; and a computer for processing the pressure signals into position-indicating output.

26. A method for tracking an eyeball, the method comprising adhering a system for sensing ocular position according to any one of claims 1 to 23 to an eyeball via tear-film adhesion; detecting/receiving acceleration signals transmitted from the two or more accelerometers; and processing the acceleration signals into position-indicating output.

27. A method for tracking an eyeball, the method comprising adhering a system for sensing ocular position according to any one of claims 1 to 23 to an eyeball via tear-film adhesion; detecting/receiving acceleration and pressure signals transmitted from the two or more accelerometers and corresponding pressure transducers; and processing the acceleration and pressure signals into position-indicating output.

* * * * *